(12) United States Patent
Liang et al.

(10) Patent No.: US 8,173,852 B1
(45) Date of Patent: May 8, 2012

(54) METHODS AND APPARATUSES FOR PRODUCING STYRENE FROM ETHYLBENZENE

(75) Inventors: Wugeng Liang, Elgin, IL (US); James A. Johnson, Burr Ridge, IL (US)

(73) Assignee: UOP LLC, Des Plaines, IL (US)

( * ) Notice: Subject to any disclaimer, the term of this patent is extended or adjusted under 35 U.S.C. 154(b) by 0 days.

(21) Appl. No.: 13/109,584

(22) Filed: May 17, 2011

(51) Int. Cl.
*C07C 5/327* (2006.01)

(52) U.S. Cl. .......................................... 585/441; 585/440
(58) Field of Classification Search .................. 585/441, 585/440
See application file for complete search history.

(56) References Cited

U.S. PATENT DOCUMENTS

| | | | |
|---|---|---|---|
| 4,914,249 A | 4/1990 | Benedict | |
| 6,037,511 A | 3/2000 | Park et al. | |
| 6,482,375 B1 | 11/2002 | van der Wal et al. | |
| 6,884,915 B2 | 4/2005 | Obayashi et al. | |
| 7,193,121 B2 | 3/2007 | Walsdorff et al. | |
| 2009/0312589 A1 | 12/2009 | Schwint et al. | |
| 2009/0318743 A1 | 12/2009 | Arnold et al. | |
| 2010/0222621 A1 | 9/2010 | Gaffney et al. | |

*Primary Examiner* — Thuan Dinh Dang
(74) *Attorney, Agent, or Firm* — Mark R Willis

(57) ABSTRACT

Embodiments of methods and apparatuses for producing styrene are provided. The method comprises the steps of introducing ethylbenzene to a first dehydrogenation reactor containing a first high activity dehydrogenation catalyst at a first predetermined inlet temperature to form a first intermediate effluent stream that comprises styrene, ethylbenzene, and hydrogen. Oxygen is added to the first intermediate effluent stream to form a first oxygenated intermediate effluent stream. The first oxygenated intermediate effluent stream is introduced to a first oxidation-reheat dehydrogenation reactor at a second predetermined inlet temperature of about 530° C. or less to form styrene. The first oxidation-reheat dehydrogenation reactor contains a first oxidation catalyst and a second high activity dehydrogenation catalyst.

8 Claims, 2 Drawing Sheets

METHODS AND APPARATUSES FOR PRODUCING STYRENE FROM ETHYLBENZENE

FIELD OF THE INVENTION

The present invention relates generally to methods and apparatuses for producing less saturated aromatic hydrocarbons from the dehydrogenation of alkylaromatic hydrocarbons, and more particularly to methods and apparatuses for producing styrene from the dehydrogenation of ethylbenzene.

BACKGROUND OF THE INVENTION

Catalytic dehydrogenation processes are commonly used for the production of less saturated aromatic hydrocarbons from the dehydrogenation of alkylaromatic hydrocarbons. One commercialized application of this process is for the conversion of ethylbenzene to styrene. The catalytic dehydrogenation of ethylbenzene to produce styrene is an endothermic equilibrium-controlled reaction that also produces hydrogen.

One conventional catalytic dehydrogenation process for the production of styrene employs a series of reactors each containing a dehydrogenation catalyst. A heated feed stream of ethylbenzene is introduced to a first reactor at a desired reaction temperature and contacts the dehydrogenation catalyst forming a product mixture of styrene and hydrogen. As the feed stream and the product mixture advance through the reactor, the temperature drops because the reaction is endothermic and the rate of conversion of ethylbenzene to styrene rapidly decreases. A lower temperature intermediate effluent stream comprising styrene, hydrogen, and unreacted ethylbenzene is removed from the first reactor, heated to a desired reaction temperature, and introduced to a second reactor for additional conversion of ethylbenzene to styrene and hydrogen. This process may be repeated using one or more additional reactors to improve the product yield. Unfortunately, the overall conversion of ethylbenzene to styrene typically only reaches about 60 to 65% with the additional reactors because the reaction is equilibrium-controlled. This results in an inefficient process with large volumes of unreacted ethylbenzene that are costly to recover and recycle.

More recently, another catalytic dehydrogenation process for the production of styrene has been employed for improving the overall conversion of ethylbenzene to styrene. The process uses a series of reactors where the first reactor of the series contains a dehydrogenation catalyst as described above, and at least one additional reactor that is a multi-catalyst reactor contains both an oxidation catalyst and a dehydrogenation catalyst. In this process, oxygen is added to the intermediate effluent stream after the first reactor but before the effluent stream is introduced to the multi-catalyst reactor. Once introduced to the multi-catalyst reactor, the intermediate effluent stream contacts the oxidation catalyst burning at least a portion of the hydrogen with oxygen to heat the intermediate effluent stream to a desired reaction temperature. The heated intermediate effluent stream contacts the dehydrogenation catalyst for additional conversion of ethylbenzene to styrene and hydrogen. Because at least a portion of the hydrogen in the intermediate effluent stream has been consumed to generate heat, ideally the equilibrium-controlled reaction of ethylbenzene to styrene and hydrogen favors the product side to improve the levels of ethylbenzene conversion. Unfortunately, an improvement in the overall ethylbenzene conversion is not realized because some of the ethylbenzene and styrene burn from contact with the oxidation catalyst in the presence of oxygen forming carbon monoxide and carbon dioxide. This has a negative impact on the performance of the dehydrogenation catalyst including reducing catalyst activity and shortening catalyst life.

Accordingly, it is desirable to provide methods and apparatuses for producing styrene with improved overall ethylbenzene conversion to styrene. Moreover, it is desirable to provide methods and apparatuses for producing styrene without negatively impacting the performance of the dehydrogenation catalyst otherwise caused from forming carbon monoxide and carbon dioxide. Furthermore, other desirable features and characteristics of the present invention will become apparent from the subsequent Detailed Description of the Invention and the appended Claims, when taken in conjunction with the accompanying drawings and this Background of the Invention.

SUMMARY OF THE INVENTION

Methods and apparatuses for producing styrene are provided herein. In accordance with an exemplary embodiment, a method for producing styrene comprises the steps of introducing ethylbenzene to a first dehydrogenation reactor containing a first high activity dehydrogenation catalyst at a first predetermined inlet temperature to form a first intermediate effluent stream that comprises styrene, ethylbenzene, and hydrogen. Oxygen is added to the first intermediate effluent stream to form a first oxygenated intermediate effluent stream. The first oxygenated intermediate effluent stream is introduced to a first oxidation-reheat dehydrogenation reactor at a second predetermined inlet temperature of about 530° C. or less to form styrene. The first oxidation-reheat dehydrogenation reactor contains a first oxidation catalyst and a second high activity dehydrogenation catalyst.

In accordance with another exemplary embodiment, a method for producing styrene is provided. The method comprises the steps of introducing ethylbenzene to a first dehydrogenation reactor containing a first high activity dehydrogenation catalyst at a first predetermined inlet temperature of about 620° C. or less to form a first intermediate effluent stream that comprises styrene, ethylbenzene, and hydrogen. The first high activity dehydrogenation catalyst has a first relative activity of about 1.5 or greater for conversion of ethylbenzene to styrene. An oxygen stream and a steam stream are combined with the first intermediate effluent stream to form a first oxygenated intermediate effluent stream. The first oxygenated intermediate effluent stream is introduced to a first oxidation-reheat dehydrogenation reactor at a second predetermined inlet temperature of about 530° C. or less to form styrene. The first oxidation-reheat dehydrogenation reactor contains an oxidation catalyst and a second high activity dehydrogenation catalyst that has a second relative activity of about 1.5 or greater for conversion of ethylbenzene to styrene.

In accordance with another exemplary embodiment, and apparatus for producing styrene is provided. The apparatus comprises a first dehydrogenation reactor containing a first high activity dehydrogenation catalyst and is configured to receive ethylbenzene at a first predetermined inlet temperature and to form a first intermediate effluent stream that comprises styrene, ethylbenzene, and hydrogen. The first dehydrogenation reactor is configured to be in fluid communication with a first oxygen source. A first oxidation-reheat dehydrogenation reactor configured to be in fluid communication with the first oxygen source and the first dehydrogenation reactor and containing a first oxidation catalyst and a second high activity dehydrogenation catalyst. The first oxidation-reheat dehydrogenation reactor is configured to receive a first oxygenated intermediate effluent stream from the first oxygen source and the first dehydrogenation reactor at a second predetermined inlet temperature to form styrene.

BRIEF DESCRIPTION OF THE DRAWINGS

Embodiments of the present invention will hereinafter be described in conjunction with the following drawing figures, wherein like numerals denote like elements, and wherein.

DETAILED DESCRIPTION

Figure 1:
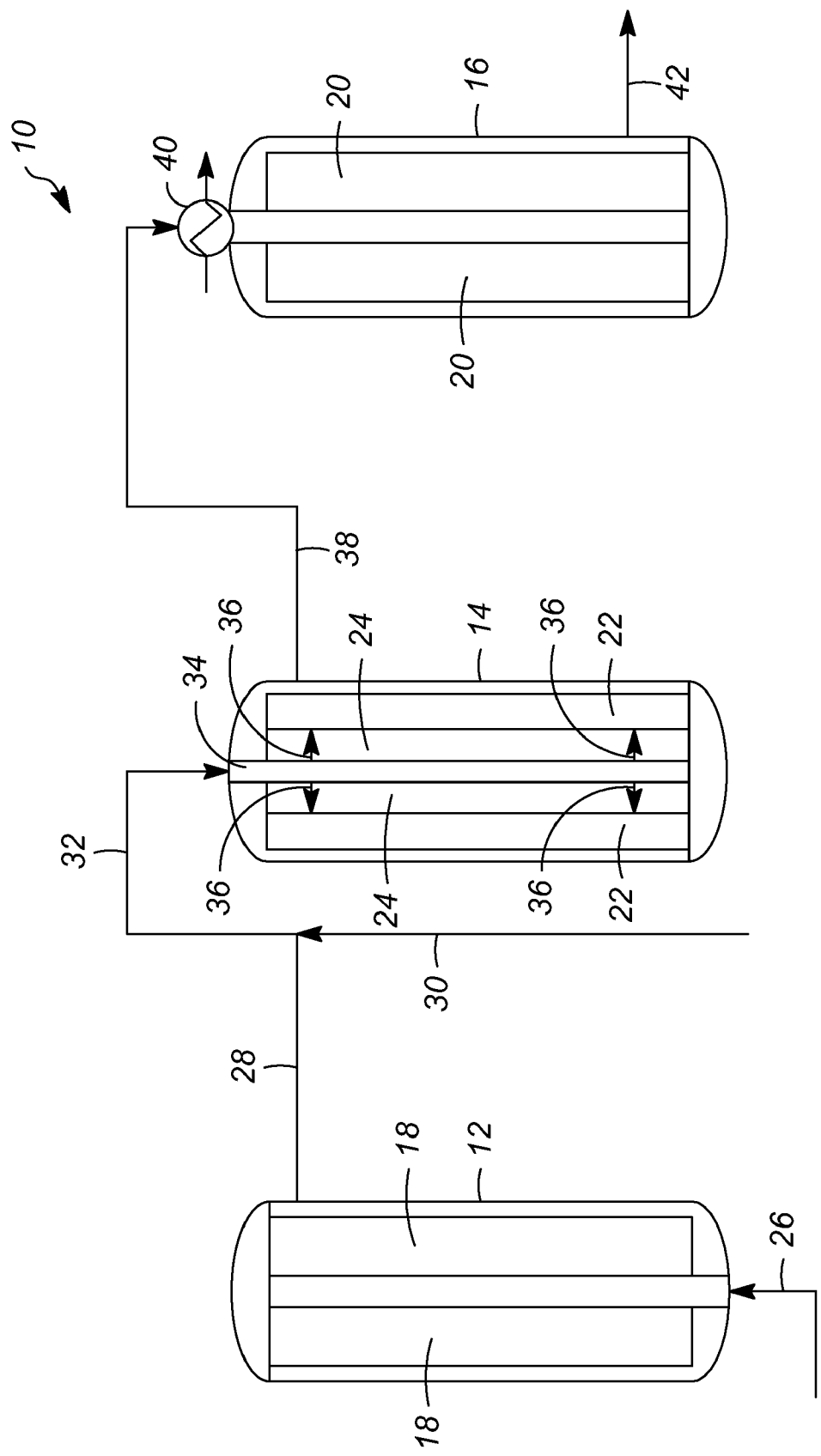
FIG. 1 schematically illustrates an apparatus for producing styrene in accordance with an exemplary embodiment.

The following Detailed Description is merely exemplary in nature and is not intended to limit the invention or the application and uses of the invention. Furthermore, there is no intention to be bound by any theory presented in the preceding Background of the Invention or the following Detailed Description.

Various embodiments contemplated herein relate to methods and apparatuses for producing styrene. Unlike the prior art, the exemplary embodiments taught herein produce a low temperature intermediate effluent stream comprising styrene, hydrogen, and unreacted ethylbenzene using a high activity dehydrogenation catalyst that increases initial conversion of ethylbenzene to styrene and substantially decreases the temperature of the stream. The low temperature or cooled intermediate effluent stream is then oxygenated to form a cooled oxygenated intermediate effluent stream that is introduced at an inlet temperature of preferably about 530° C. or less to an oxidation-reheat dehydrogenation reactor. The oxidation-reheat dehydrogenation reactor contains an oxidation catalyst and a high activity dehydrogenation catalyst. The cooled oxygenated intermediate effluent stream contacts the oxidation catalyst to combust at least a portion of hydrogen contained in the stream to generate heat and produce a heated hydrogen-lean intermediate effluent stream. The inventors have found that the combustion selectivity of ethylbenzene and styrene in contact with an oxidation catalyst in the presence of oxygen is temperature sensitive and substantially decreases with lower temperatures. Therefore, introducing the cooled oxygenated intermediate effluent stream to the oxidation-reheat dehydrogenation reactor at lower inlet temperatures will decrease the combustion selectivity of ethylbenzene and styrene in favor of burning hydrogen. By introducing the oxygenated intermediate effluent stream to the oxidation-reheat dehydrogenation reactor at a temperature of about 530° C. or less, the combustion selectivity of styrene and ethylbenzene is low and the combustion selectivity of hydrogen is high, thereby burning more hydrogen to form water and much less ethylbenzene and styrene to substantially reduce the formation of carbon monoxide and carbon dioxide. The heated hydrogen-lean intermediate effluent stream contacts the high activity dehydrogenation catalyst in the oxidation-reheat dehydrogenation reactor to produce additional styrene. Because at least a portion of hydrogen from the cooled oxygenated intermediate effluent stream was consumed to generate heat, there is less hydrogen present in the heated hydrogen-lean intermediate effluent stream and the equilibrium-controlled reaction shifts towards higher conversions of ethylbenzene to styrene. Moreover, the high activity dehydrogenation catalyst in the oxidation-reheat dehydrogenation reactor facilitates higher conversion of ethylbenzene to styrene even at lower inlet temperatures. Furthermore, because there is substantially less combustion of ethylbenzene and styrene in the oxidation-reheat dehydrogenation reactor, there is very little carbon monoxide and carbon dioxide present in the heated hydrogen-lean intermediate effluent stream and therefore, the performance of the high activity dehydrogenation catalyst is not negatively impacted. Accordingly, relatively more ethylbenzene can be effectively converted to styrene than in conventional processes.

Referring to FIG. 1, a schematic depiction of an apparatus 10 for producing styrene from the catalytic dehydrogenation of ethylbenzene in accordance with an exemplary embodiment is provided. The apparatus 10 comprises a first dehydrogenation reactor 12, an oxidation-reheat dehydrogenation reactor 14, and a second dehydrogenation reactor 16. Although two dehydrogenation reactors are shown, it is to be understood that one dehydrogenation reactor or more than two dehydrogenation reactors may be used. Moreover, although one oxidation-reheat dehydrogenation reactor is shown, it is to be understood that more than one oxidation-reheat dehydrogenation reactor may be used.

The first and second dehydrogenation reactors 12 and 16 and the oxidation-reheat dehydrogenation reactor 14 each comprise at least one dehydrogenation catalyst bed 18, 20, and 22, respectively, containing a high activity dehydrogenation catalyst. Various dehydrogenation catalysts for converting ethylbenzene to styrene are well known in the art and typically include iron oxide and/or potassium oxide, such as, for example, $FeO_3$, $K_2O$, and the like, and optionally one or more promoters, such as, for example, chromium oxide, cesium oxide, molybdenum oxide, magnesium oxide, aluminum oxide, vanadium oxide, calcium oxide, and the like. However, the relative activity of these dehydrogenation catalysts for converting ethylbenzene to styrene can vary significantly. The relative activity as used herein refers to the relative effectiveness of the catalyst to convert ethylbenzene to styrene under dehydrogenation conditions. The relative activity of a dehydrogenation catalyst is determined by introducing an ethylbenzene feed stream to a reactor containing the dehydrogenation catalyst where the ethylbenzene feed stream is introduced to the reactor at an inlet temperature of about 600° C., an inlet pressure of about 0.8 atmospheres, a liquid hourly space velocity (LHSV) of about $1.0$ $hr^{-1}$, a steam/oil ratio of about 1.25 (wt/wt), and then the conversion of ethylbenzene to styrene is determined from the resulting product effluent. Under these conditions, a dehydrogenation catalyst providing about 34.3% ethylbenzene conversion has a relative activity of about 1.0, a dehydrogenation catalyst providing about 39.1% ethylbenzene conversion has a relative activity of about 1.5, and a dehydrogenation catalyst providing about 41.9% ethylbenzene conversion has a relative activity of about 2.0. A relative activity of about 1.0 represents an average or typically effective dehydrogenation catalyst, and a relative activity of greater than 1.0 represents a more highly effective dehydrogenation catalyst. Dehydrogenation catalysts that have a relative activity of about 1.5 or greater can be achieved by varying catalyst composition or its geometric shapes. In accordance with an exemplary embodiment, the relative activity of the high activity dehydrogenation catalyst contained in the reactors 12, 14, and 16 is about 1.5 or greater, and more preferably is about 2.0 or greater. Accordingly, the high activity dehydrogenation catalyst is highly effective at converting ethylbenzene to styrene and preferably provides more rapid or higher initial levels of ethylbenzene conversion even at relatively lower inlet temperatures than other dehydrogenation catalyst having lower relative activity.

The oxidation-reheat dehydrogenation reactor 14 also contains an oxidation catalyst bed 24 that contains an oxidation catalyst. Oxidation catalysts for combusting hydrogen in the presence of oxygen to form water are well known in the art and are often based on tin and/or platinum, such as, for example, tin and alkali-promoted platinum, tin/alkali-doped alumina-supported platinum, and the like. Other oxidation catalysts for combusting hydrogen in the presence of oxygen known to those skilled in the art may also be used.

As illustrated, a feed stream 26 of ethylbenzene with steam is introduced to the first dehydrogenation reactor 12 and contacts the high activity dehydrogenation catalyst to convert a portion of ethylbenzene to styrene and hydrogen, and form a first intermediate effluent stream 28 that comprises styrene, ethylbenzene, and hydrogen. Because the first dehydrogenation reactor 12 contains the high activity dehydrogenation catalyst, the feed stream 26 can be introduced to the first dehydrogenation reactor 12 at a lower inlet temperature compared with other conventional catalytic dehydrogenation processes for styrene production and preferably still achieve higher initial levels of ethylbenzene conversion. Moreover, since the conversion of ethylbenzene to styrene is endothermic, achieving higher initial levels of ethylbenzene conversion further reduces the overall temperature. In accordance with an exemplary embodiment, the feed stream 26 is introduced to the first dehydrogenation reactor 12 at a first predetermined inlet temperature of from about 550 to about 620° C., and preferably from about 570 to 600° C. In accordance with another exemplary embodiment, the first intermediate effluent stream 28 is removed from the first dehydrogenation reactor 12 at an outlet temperature of from about 480 to about 540° C.

An oxygen stream, e.g., stream of air or the like, and steam stream 30 are passed along and combined with the first intermediate effluent stream 28. The oxygen oxygenates the first intermediate effluent stream 28 to form a first oxygenated intermediate effluent stream 32. The added steam preferably enhances the activity, selectivity, and/or stability of the high activity dehydrogenation catalyst that will be subsequently contacted by the intermediate effluent stream in the oxidation-reheat dehydrogenation reactor 14 and the second dehydrogenation reactor 16. In an exemplary embodiment, the oxygen and steam stream 30 are at conditions and temperatures effective to further cool the first intermediate effluent stream 28 if needed to form the first oxygenated intermediate effluent stream 32 having a second predetermined inlet temperature of about 530° C. or less, preferably of from about 480 to about 530° C., more preferably of from about 480 to about 510° C., and most preferably of from about 485 to about 500° C.

The first oxygenated intermediate effluent stream 32 is introduced to the oxidation-reheat dehydrogenation reactor 14 at the second predetermined inlet temperature. As illustrated, the oxidation catalyst bed 24 is configured as an elongated inner ring surrounded concentrically by the dehydrogenation catalyst bed 22 that is configured as an elongated outer ring. A radial feed distribution screen 34 is disposed within the oxidation catalyst bed 24. The first oxygenated intermediate effluent stream 32 advances along the radial feed distribution screen 34 and is radially introduced to the oxidation catalyst bed 24. The first oxygenated intermediate effluent stream 32 contacts the oxidation catalyst to burn hydrogen in the presence of oxygen to form water and generate heat, thereby forming a first heated hydrogen-lean intermediate effluent stream 36. By keeping the inlet temperature of the first oxygenated intermediate effluent stream 32 at about 530° C. or less, the resulting temperatures in the oxidation catalyst bed 24 are relatively low such that the combustion selectivity of the ethylbenzene and styrene is low. This facilitates limiting the amount of carbon monoxide and carbon dioxide produced when ethylbenzene and styrene contact the oxidation catalyst in the presence of oxygen. Accordingly, the amounts of carbon monoxide and carbon dioxide present in the first heated hydrogen-lean intermediate effluent stream 36 are low.

In an exemplary embodiment, the first heated hydrogen-lean intermediate effluent stream 36 is introduced to the dehydrogenation catalyst bed 22 at a third predetermined temperature of from about 550 to about 620° C., and preferably from about 570 to about 600° C. The first heated hydrogen-lean intermediate effluent stream 36 contacts the high activity dehydrogenation catalyst to convert a portion of ethylbenzene to styrene and form a second intermediate effluent stream 38 that comprises styrene, ethylbenzene, and hydrogen. Because at least a portion of hydrogen from the first oxygenated intermediate effluent stream 32 was consumed to generate heat in the oxidation catalyst bed 24, there is less hydrogen present in the first heated hydrogen-lean effluent intermediate stream 36 and the equilibrium-controlled reaction shifts towards higher conversions of ethylbenzene to styrene. Moreover, because there is a low amount of carbon monoxide and carbon dioxide present in the first heated hydrogen-lean effluent intermediate stream 36, the performance of the high activity dehydrogenation catalyst in the dehydrogenation catalyst bed 22 is not negatively impacted. Furthermore, the high activity dehydrogenation catalyst is highly effective at converting ethylbenzene to styrene even at lower inlet temperatures and therefore, facilitates higher ethylbenzene conversion. Accordingly, relatively more ethylbenzene can be converted to styrene than in conventional processes.

The second intermediate effluent stream 38 passes from the oxidation-reheat dehydrogenation reactor 14 to a heat exchanger 40. In an exemplary embodiment, the second intermediate effluent stream 38 leaves the oxidation-reheat dehydrogenation reactor 14 at an outlet temperature of from about 500 to about 560° C. The second intermediate effluent stream 38 is heated by indirect heat exchange via the heat exchanger 40 to a fourth predetermined inlet temperature of from about 550 to about 620° C., and preferably from about 570 to 600° C. The second intermediate effluent stream 38 is then introduced to the second dehydrogenation reactor 16 at the fourth predetermined inlet temperature. The second intermediate effluent stream 38 contacts the high activity dehydrogenation catalyst to convert a portion of the ethylbenzene to styrene forming a third effluent stream 42 that comprises styrene, ethylbenzene, and hydrogen. In a preferred embodiment, the apparatus 10 provides an overall conversion of ethylbenzene in the feed stream 26 to styrene in the third effluent stream 42 of about 73% or greater.

Figure 2:
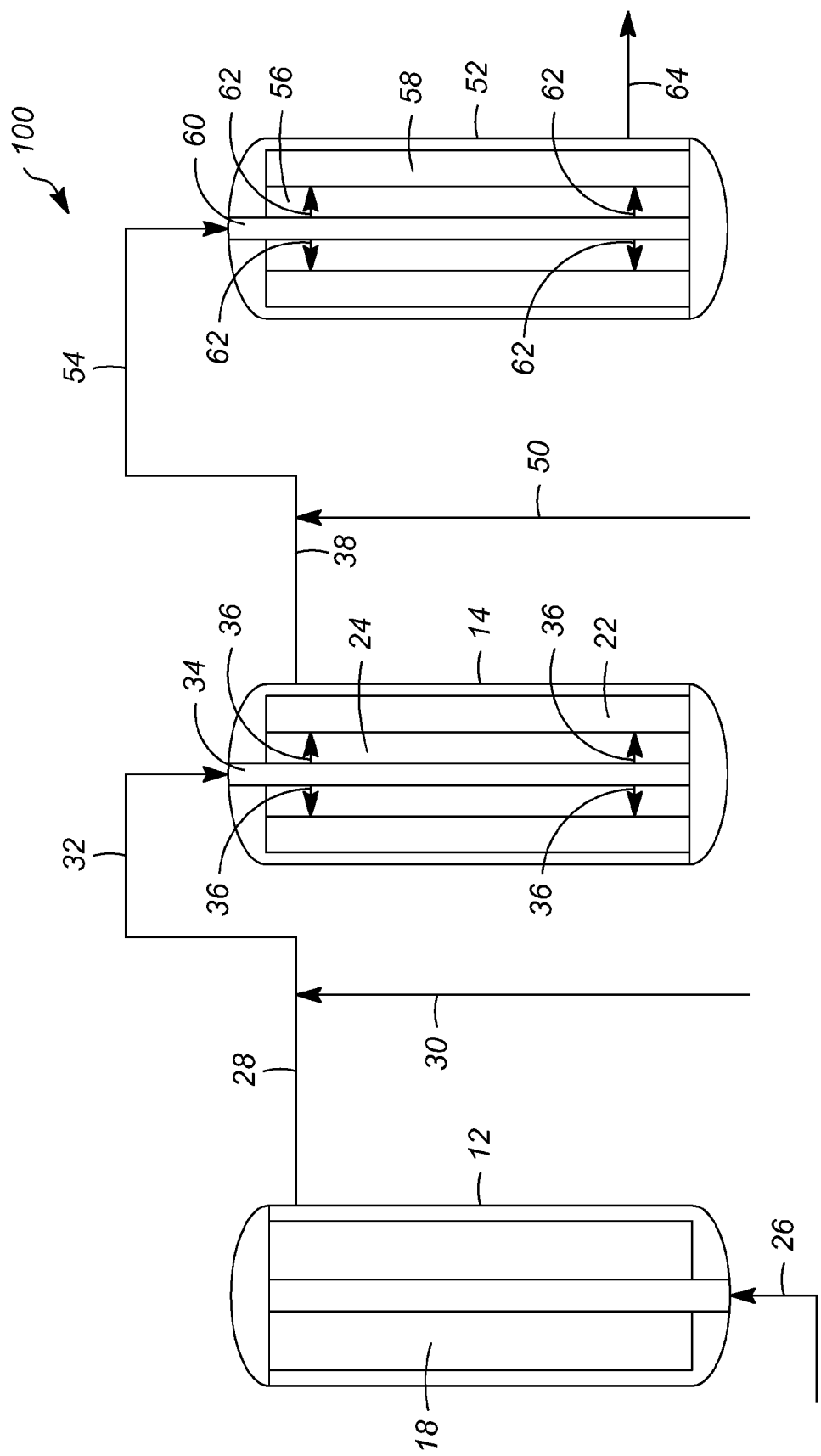
FIG. 2 schematically illustrates an apparatus for producing styrene in accordance with another exemplary embodiment.

Referring to FIG. 2, a schematic depiction of an apparatus 100 for producing styrene from the catalytic dehydrogenation of ethylbenzene in accordance with another exemplary embodiment is provided. The apparatus 100 comprises the first dehydrogenation reactor 12, the oxygen and steam stream 30, and the first oxidation-reheat dehydrogenation reactor 14 as discussed in the foregoing paragraphs in relation to FIG. 1. The apparatus 100 further comprises a second oxygen and steam stream 50 and a second oxidation-reheat dehydrogenation reactor 52. As discussed above, the feed stream 26 of ethylbenzene contacts the high activity dehydrogenation catalyst in the first dehydrogenation reactor 12, is oxygenated via the oxygen and steam stream 30, and contacts the oxidation catalyst and the high activity dehydrogenation catalyst in the first oxidation-reheat dehydrogenation reactor 14 to form the second intermediate effluent stream 38.

The second intermediate effluent stream 38 is removed from the first oxidation-reheat dehydrogenation reactor 14 at an outlet temperature of preferably from about 500 to about 560° C. The second oxygen and steam stream 50 combine with the second intermediate effluent stream 38 to form a second oxygenated intermediate effluent stream 54. In an exemplary embodiment, the second oxygen and steam stream 50 are at conditions and temperatures effective to further cool the second intermediate effluent stream 38 if needed to form the second oxygenated intermediate effluent stream 54 having a fourth predetermined inlet temperature of about 530° C. or less, preferably of from about 480 to about 530° C., more preferably of from about 480 to about 510° C., and most preferably of from about 485 to about 500° C.

The second oxygenated intermediate effluent stream 54 is introduced to the second oxidation-reheat dehydrogenation reactor 52 at the fourth predetermined inlet temperature. As illustrated, the second oxidation-reheat dehydrogenation reactor 52 is configured similar to the first oxidation-reheat dehydrogenation reactor 14 and comprises an oxidation catalyst bed 56 containing an oxidation catalyst, a dehydrogenation catalyst bed 58 that concentrically surrounds the oxidation catalyst bed 56 and contains a high activity dehydrogenation catalyst, and a radial feed distribution screen 60 that is disposed within the oxidation catalyst bed 56. The second oxygenated intermediate effluent stream 54 advances along the radial feed distribution screen 60 and is radially introduced to the oxidation catalyst bed 56. The second oxygenated intermediate effluent stream 54 contacts the oxidation catalyst to burn hydrogen in the presence of oxygen to form water and generate heat, thereby forming a second heated hydrogen-lean intermediate effluent stream 62. By keeping the inlet temperature of the second oxygenated intermediate effluent stream 54 at about 530° C. or less, the resulting temperatures in the oxidation catalyst bed 56 are relatively low such that the combustion selectivity of ethylbenzene and styrene is low. This facilitates limiting the amount of carbon monoxide and carbon dioxide produced when the ethylbenzene and styrene contact the oxidation catalyst in the presence of oxygen. Accordingly, the amounts of carbon monoxide and carbon dioxide present in the second heated hydrogen-lean intermediate effluent stream 62 are low.

In an exemplary embodiment, the second heated hydrogen-lean intermediate effluent stream 62 is introduced to the dehydrogenation catalyst bed 58 at a fifth predetermined temperature of from about 550 to about 620° C., and preferably from about 570 to about 600° C. The second heated hydrogen-lean intermediate effluent stream 62 contacts the high activity dehydrogenation catalyst to convert a portion of ethylbenzene to styrene and form a third effluent stream 64 that comprises styrene, ethylbenzene, and hydrogen. Because at least a portion of hydrogen from the second oxygenated intermediate effluent stream 54 was consumed to generate heat in the oxidation catalyst bed 56, there is less hydrogen present in the second heated hydrogen-lean intermediate effluent stream 62 and the equilibrium-controlled reaction shifts towards higher conversions of ethylbenzene to styrene. Moreover, because there is a low amount of carbon monoxide and carbon dioxide present in the second heated hydrogen-lean intermediate effluent stream 62, the performance of the high activity dehydrogenation catalyst in the dehydrogenation catalyst bed 58 is not negatively impacted. Furthermore, the high activity dehydrogenation catalyst is highly effective at converting ethylbenzene to styrene even at lower inlet temperatures and therefore, facilitates higher ethylbenzene conversion. Accordingly, relatively more ethylbenzene can be converted to styrene. In a preferred embodiment, the apparatus 100 provides an overall conversion of ethylbenzene from the feed stream 26 to styrene in the third effluent stream 64 of about 75% or greater.

Accordingly, methods and apparatuses for producing styrene have been described. Unlike the prior art, the exemplary embodiments taught herein use a high activity dehydrogenation catalyst to convert an ethylbenzene feed stream to a cooled intermediate effluent stream comprising styrene, hydrogen, and unreacted ethylbenzene. The cooled intermediate effluent stream is oxygenated to form a cooled oxygenated intermediate effluent stream that is introduced to an oxidation-reheat dehydrogenation reactor containing an oxidation catalyst and a high activity dehydrogenation catalyst. The cooled oxygenated intermediate effluent stream contacts the oxidation catalyst to combust at least a portion of hydrogen contained in the stream to generate heat and produce a heated hydrogen-lean intermediate effluent stream. The combustion selectivity of ethylbenzene and styrene is temperature sensitive and substantially decreases with lower temperatures. Accordingly, the cooled oxygenated intermediate effluent stream, which has a lower inlet temperature when introduced to the oxidation-reheat dehydrogenation reactor, has a decreased combustion selectivity of ethylbenzene and styrene in favor of burning hydrogen, thereby burning more hydrogen to form water and much less ethylbenzene and styrene to substantially reduce the formation of carbon monoxide and carbon dioxide. The heated hydrogen-lean intermediate effluent stream then contacts the high activity dehydrogenation catalyst in the oxidation-reheat dehydrogenation reactor to produce additional styrene. Because at least a portion of hydrogen from the cooled oxygenated intermediate effluent stream was consumed to generate heat, there is less hydrogen present in the heated hydrogen-lean intermediate effluent stream and the equilibrium-controlled reaction shifts towards higher conversions of ethylbenzene to styrene. Moreover, the high activity dehydrogenation catalyst in the oxidation-reheat dehydrogenation reactor facilitates higher conversion of ethylbenzene to styrene even at lower inlet temperatures. Furthermore, because there is substantially less combustion of ethylbenzene and styrene in the oxidation-reheat dehydrogenation reactor, there is very little carbon monoxide and carbon dioxide present in the heated hydrogen-lean intermediate effluent stream and therefore, the performance of the high activity dehydrogenation catalyst is not negatively impacted. Accordingly, relatively more ethylbenzene can be effectively converted to styrene than in conventional processes.

While at least one exemplary embodiment has been presented in the foregoing Detailed Description, it should be appreciated that a vast number of variations exist. It should also be appreciated that the exemplary embodiment or exemplary embodiments are only examples, and are not intended to limit the scope, applicability, or configuration of the invention in any way. Rather, the foregoing Detailed Description will provide those skilled in the art with a convenient road map for implementing an exemplary embodiment of the invention, it being understood that various changes may be made in the function and arrangement of elements described in an exemplary embodiment without departing from the scope of the invention as set forth in the appended Claims and their legal equivalents.

What is claimed is:

1. A method for producing styrene, the method comprising the steps of:
    introducing ethylbenzene to a first dehydrogenation reactor containing a first high activity dehydrogenation catalyst that has a relative activity of about 1.5 or greater at a first predetermined inlet temperature of from about 550 to about 620° C. to form a first intermediate effluent stream that comprises styrene, ethylbenzene, and hydrogen;

adding oxygen to the first intermediate effluent stream to form a first oxygenated intermediate effluent stream; and introducing the first oxygenated intermediate effluent stream to a first oxidation-reheat dehydrogenation reactor at a second predetermined inlet temperature of about 510° C. or less to form styrene, wherein the first oxidation-reheat dehydrogenation reactor contains a first oxidation catalyst and a second high activity dehydrogenation catalyst that has a relative activity of about 1.5 or greater, wherein the step of introducing the first oxygenated intermediate effluent stream includes contacting the first oxygenated intermediate effluent stream with the first oxidation catalyst contained in an oxidation bed to form a first heated hydrogen-lean intermediate effluent stream, and contacting the first heated hydrogen-lean intermediate effluent stream with the second high activity dehydrogenation catalyst contained in a dehydrogenation bed to form styrene.

2. The method according to claim 1, wherein the step of introducing the first oxygenated intermediate effluent stream includes introducing the first oxygenated intermediate effluent stream to the first oxidation-reheat dehydrogenation reactor containing the second high activity dehydrogenation catalyst that has a relative activity of about 2 or greater.

3. The method according to claim 1, wherein the step of introducing ethylbenzene includes forming the first intermediate effluent stream at an outlet temperature of from about 480 to about 540° C.

4. The method according to claim 1, wherein the step of introducing the first oxygenated intermediate effluent stream includes introducing the first oxygenated intermediate effluent stream at the second predetermined inlet temperature of from about 480 to about 510° C.

5. The method according to claim 1, wherein the step of introducing ethylbenzene includes forming the first intermediate effluent stream at an outlet temperature that is greater than the second predetermined inlet temperature, and wherein the step of adding oxygen includes adding oxygen and steam to the first intermediate effluent stream at temperatures effective to cool the first intermediate effluent stream and form the first oxygenated intermediate effluent stream at the second predetermined inlet temperature.

6. The method according to claim 1, wherein the step of introducing the first oxygenated intermediate effluent stream includes forming the first heated hydrogen-lean intermediate effluent stream at a third predetermined temperature of from about 550 to about 620° C., and introducing the first heated hydrogen-lean intermediate effluent stream to the dehydrogenation bed at the third predetermined temperature for contacting the second high activity dehydrogenation catalyst.

7. The method according to claim 1, wherein the step of introducing the first oxygenated intermediate effluent stream includes forming a second intermediate effluent stream comprising styrene, ethylbenzene, and hydrogen, and the method further comprising the steps of:

introducing the second intermediate effluent stream to a heat exchanger for indirect heating to form a heated second intermediate effluent stream; and introducing the heated second intermediate effluent stream to a second dehydrogenation reactor containing a third high activity dehydrogenation catalyst at conditions effective to form styrene.

8. The method according to claim 1, wherein the step of introducing the first oxygenated intermediate effluent stream includes forming a second intermediate effluent stream comprising styrene, ethylbenzene, and hydrogen, and the method further comprising the steps of:

adding oxygen to the second intermediate effluent stream to form a second oxygenated intermediate effluent stream; and introducing the second oxygenated intermediate effluent stream to a second oxidation-reheat dehydrogenation reactor at a fourth predetermined inlet temperature of about 530° C. or less to form styrene, wherein the second oxidation-reheat dehydrogenation reactor contains a second oxidation catalyst and a fourth high activity dehydrogenation catalyst.

* * * * *